United States Patent
Yonezu et al.

(10) Patent No.: US 8,806,918 B2
(45) Date of Patent: Aug. 19, 2014

(54) GAS SENSOR AND MANUFACTURING METHOD THEREFOR

(75) Inventors: Kunihiko Yonezu, Inabe (JP); Hisaharu Nishio, Tokai (JP); Takaya Yoshikawa, Kasugai (JP); Tomohiro Tajima, Kasugai (JP); Masao Tsuzuki, Kakamigahara (JP)

(73) Assignee: NGK Spark Plug Co., Ltd., Aichi (JP)

( * ) Notice: Subject to any disclaimer, the term of this patent is extended or adjusted under 35 U.S.C. 154(b) by 176 days.

(21) Appl. No.: 13/224,283

(22) Filed: Sep. 1, 2011

(65) Prior Publication Data

US 2012/0055234 A1    Mar. 8, 2012

(30) Foreign Application Priority Data

Sep. 3, 2010 (JP) ................................ 2010-198034

(51) Int. Cl.
*G01N 27/403* (2006.01)
(52) U.S. Cl.
USPC ........................................ 73/31.05; 204/424
(58) Field of Classification Search
USPC .......... 73/31.05, 23.31; 29/883; 204/424–431
See application file for complete search history.

(56) References Cited

U.S. PATENT DOCUMENTS 5,820,739 A * 10/1998 Graser et al. ................... 204/421
6,068,746 A * 5/2000 Kojima et al. ................ 204/421
6,427,316 B1 * 8/2002 Shinjo et al. ................. 29/602.1
7,425,153 B1 * 9/2008 Miller ........................... 439/578
2008/0139029 A1 * 6/2008 Tsuji et al. .................... 439/271
2009/0023338 A1 * 1/2009 He et al. ........................ 439/607
2009/0126456 A1   5/2009 Matsuo et al.
2012/0018305 A1   1/2012 Yoshikawa et al.

FOREIGN PATENT DOCUMENTS

| DE | 102008055129 A1 | 7/2010 |
| DE | 112004000050 B4 | 6/2011 |
| EP | 0828156 A2 | 3/1998 |
| JP | 10-132779 A | 5/1998 |
| JP | 3873390 B2 | 1/2007 |
| JP | 2011-131090 | 6/2011 |

* cited by examiner

Primary Examiner — Daniel S Larkin
Assistant Examiner — Irving A Campbell
(74) Attorney, Agent, or Firm — Sughrue Mion, PLLC

(57) ABSTRACT

A gas sensor (200) includes a gas sensor element (10) extending in an axial direction (O), having a detection portion (11) provided at a front end thereof, and having electrode pads (12a) provided at a rear end thereof; connection terminals (31, 32) electrically connected to the respective electrode pads; and a cover (60, 61) covering the rear end of the gas sensor element and the connection terminals. The cover integrally has a connector portion (63) having an opening (63b) which allows an external connector to be inserted thereinto and removed therefrom in a predetermined direction, and has a connector terminal member (120) which can be inserted into the opening. The connector terminal member has a plurality of connector terminals (70) to be electrically connected to the respective connection terminals, and an insulator (121) integrally molded with the connector terminals. Also disclosed is a method for manufacturing the gas sensor.

6 Claims, 6 Drawing Sheets

GAS SENSOR AND MANUFACTURING METHOD THEREFOR

BACKGROUND OF THE INVENTION

1. Field of the Invention

The present invention relates to a gas sensor having a gas sensor element for detecting the concentration of a particular gas, and to a manufacturing method therefor.

2. Description of the Related Art

A gas sensor is mounted to an intake system (e.g., an intake pipe or an intake manifold) of an internal combustion engine, such as a diesel engine or a gasoline engine, for controlling, for example, the condition of combustion by monitoring the concentration of a particular gas. Conventionally, such a gas sensor has the following structure: a gas detection element is held in a housing made of metal, and connection terminals, a separator, etc., provided at a proximal side (rear side) of the housing are protected with a tubular cover made of metal. The gas detection element has a cell in which a solid electrolyte and a pair of electrodes are provided. The gas detection element has electrode pads formed at its rear end for electrical communication with respective electrodes. The connection terminals are electrically connected to the respective electrode pads. An electromotive force is generated depending on a difference in concentration of a particular gas at the respective electrodes and output from the connection terminals.

However, the tubular cover made of metal involves a problem in that, since the structure is intricate, manufacture or assembly consumes time and labor. In order to cope with the problem, a structure described in Patent Document 1 has been developed in which a base member made of resin is connected to a proximal end portion of the housing. The base member of Patent Document 1 has a connector portion in which the connection terminals are disposed in an inserted manner. An external connector is inserted into the connector portion, thereby establishing an electrical connection to an external system.

Meanwhile, in order to mitigate impact imposed on a colliding object with which a vehicle having an internal combustion engine collides, a clearance must be provided between the hood and engine parts. In this connection, preferably, the length of outward projection of the gas sensor from the intake pipe is shortened.

[Patent Document 1] Japanese Patent Application Laid-Open (kokai) No. H10-132779

3. Problems to be Solved by the Invention

Since a plurality of the above-mentioned connection terminals are provided in the connector portion, the connection terminals must be electrically insulated from one another. However, in the sensor described in Patent Document 1, when the connection terminals are to be attached afterward to the connector portion made of resin, the connection terminals must be press-fitted one by one into respective slits provided in the connector portion, resulting in reduced productivity. In the case where the connection terminals are insert-molded to the connector portion, a mold for the connector portion must have sufficient dimensional accuracy, and the structure of the mold becomes complicated, leading to increased cost.

SUMMARY OF THE INVENTION

Thus, an object of the present invention is to provide a gas sensor which enables improved productivity and reduced manufacturing costs by means of preparing a connector terminal member to be electrically connected to connection terminals, as a separate component, as well as a manufacturing method therefor.

The above object has been achieved, in a first aspect of the invention, by providing a gas sensor which comprises a gas sensor element extending in an axial direction, having a detection portion provided at a front end thereof for detecting a particular gas component in a gas to be measured, and having electrode pads provided at a rear end thereof; connection terminals electrically connected to the respective electrode pads; and a cover covering the rear end of the gas sensor element and the connection terminals. The cover integrally has a connector portion having an opening which allows an external connector to be inserted thereinto and removed therefrom in a predetermined direction, and has a connector terminal member which can be inserted into the opening. The connector terminal member has a plurality of connector terminals electrically connected to the respective connection terminals, and an insulator integrally molded with the connector terminals and adapted to insulate the connector terminals from one another.

According to the thus-configured gas sensor, the connector terminal member, in which a plurality of the connector terminals are integrated with the insulator, is prepared as a separate component separately from the connection terminals. The connector terminal member is connected afterward to the connection terminals, thereby eliminating the need to press-fit the connection terminals (or the connector terminals) afterward one by one to the cover (the connector portion) and thus improving productivity. Also, since there is no need to insert-mold the connection terminals to the cover (the connector portion), a mold for the cover does not need to have high dimensional accuracy, and the structure of the mold becomes simple, thereby reducing manufacturing costs.

Furthermore, by utilizing the opening of the connector portion through which an external connector is inserted and removed, the connector terminal member is inserted through the opening in the insertion/removal direction of the external connector, whereby the cover does not need to have another hole for inserting the connector terminal member. Thus, the structure of the cover (the connector portion) becomes simple, and the number of components is reduced.

The external connector is adapted to connect the gas sensor to a circuit or the like which drives and controls the gas sensor.

In a preferred embodiment, the connector terminals are bent.

In the case where the connector portion and the connector terminal member are integrally formed with each other, it is very difficult to press-fit bent connection terminals afterward to the connector portion. However, when the connector portion and the connector terminal member are separate bodies, bent connector terminals can be used.

When the cover is formed in a configuration such that the connector terminal member can be inserted into the connector portion from a radial direction, bending the connector terminals in the axial direction allows the center of a connector to be lowered. Accordingly, the axial height of the gas sensor can be lowered, whereby the length of projection of the gas sensor from a body to which the gas sensor is mounted (hereinafter referred to as a mounting body) can be shortened. Also, bending the connector terminals in a radial direction yields the following advantage: while intervals of the connector terminals are narrowed on a side toward the one ends of the connection terminals to be connected to the connector terminals so as to allow the gas sensor to be reduced in size, intervals of the connector terminals on a side opposite the one ends are widened so as to stabilize connection to an external connector.

In yet another preferred embodiment, the insulator has a flange portion which traces an inner surface of the opening.

According to the thus-configured gas sensor, when the connector terminal member is inserted into the opening, the flange portion traces the inner surface of the opening. That is, the flange portion has an outer peripheral shape and size complimentary to that of the inner peripheral surface of the opening so as to snugly fit into the opening. Thus, the connector terminal member is reliably positioned, thereby improving the reliability of connection.

In a second aspect, the present invention provides a method for manufacturing a gas sensor which comprises a gas sensor element extending in an axial direction, having a detection portion provided at a front end thereof for detecting a particular gas component in a gas to be measured, and having electrode pads provided at a rear end thereof; connection terminals electrically connected to the respective electrode pads; and a cover covering the rear end of the gas sensor element and the connection terminals and integrally having a connector portion having an opening which allows an external connector to be inserted thereinto and removed therefrom in a predetermined direction, the method comprising a connector-terminal-member insertion step of inserting a connector terminal member having a plurality of connector terminals and an insulator integrally molded with the connector terminals and adapted to insulate the connector terminals from one another, into the opening of the cover from the predetermined direction so as to insert the connector terminal member into the cover in a state in which the connector terminals are electrically connected to the respective connection terminals.

According to the above method for manufacturing a gas sensor, the connector terminal member, in which a plurality of the connector terminals are integrated with the insulator, is prepared as a separate component. The connector terminal member is connected afterward to the connection terminals, thereby eliminating the need to press-fit the connection terminals (or the connector terminals) afterward one by one to the cover (the connector portion) and thus improving productivity. Also, since there is no need to insert-mold the connection terminals to the cover (the connector portion), a mold for the cover does not need to have high dimensional accuracy. Thus, the structure of the mold becomes simple, thereby reducing manufacturing costs.

In a preferred embodiment, the method for manufacturing a gas sensor of the present invention further comprises an integration molding step of insert-molding, to the insulator, a connector terminal cluster in which a plurality of the connector terminals are integrally connected to a joint at their one ends so as to be held and spaced apart from one another, for integrally molding the insulator with the connector terminal cluster in a condition in which the joint is exposed, and a joint cutting-off step of cutting off, from the connector terminals, the joint which has been exposed in the integration molding step, thereby yielding the connector terminal member.

According to the above manufacturing method for the connector terminal member, there is no need to arrange a plurality of the connector terminals at predetermined intervals within a mold of insert molding. Rather, subjecting a single connector terminal cluster (a plurality of the connector terminals and the joint) to insert molding suffices. Thus, productivity is improved. Also, since the joint holds the connector terminals at predetermined intervals, the accuracy of the connector terminal member is improved.

EFFECT OF THE INVENTION

According to the present invention, the connector terminal member to be electrically connected to the connection terminals is prepared as a separate component, whereby gas sensor productivity can be improved, and manufacturing costs can be reduced.

DESCRIPTION OF REFERENCE NUMERALS

Figure 1:
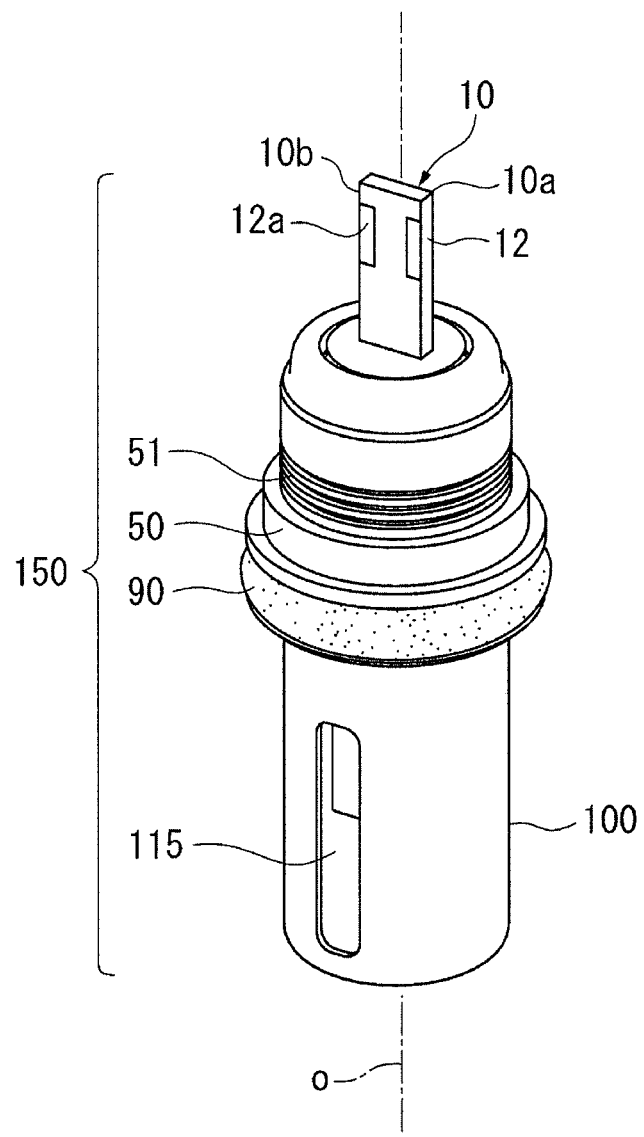
FIG. 1 is a perspective view of an element assembly held within a gas sensor according to a first embodiment of the present invention.

Reference numerals used to identify various structural features in the drawings include the following.
200, 220: gas sensor
10: gas sensor element
11: detection portion
12a: electrode pad
31, 32: connection terminal
60, 61: cover (cover body)
63: connector portion
63b: opening (of connector portion)
63i: inner surface of opening (of connector portion)
70: connector terminal
70e: one end of connector terminal
70x: connector terminal cluster
71: joint
120: connector terminal member
121: insulator
121f: flange portion (of insulator)
O: direction of axis

DETAILED DESCRIPTION OF THE PREFERRED EMBODIMENTS

Embodiments of the present invention will next be Described by reference to the drawings. However, the present invention should not be construed as being limited thereto.

Figure 2:
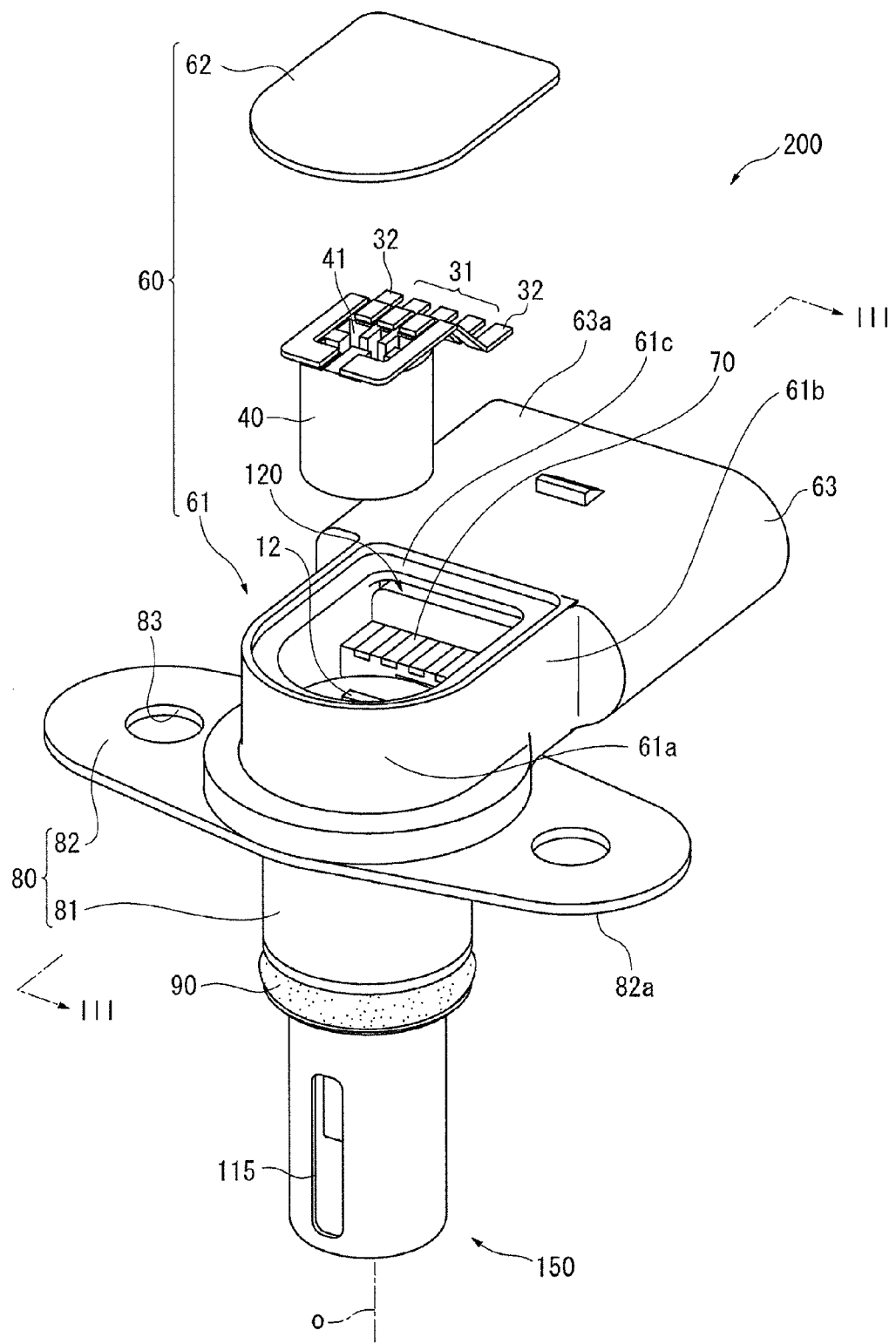
FIG. 2 is a perspective view showing the configuration of the gas sensor according to the first embodiment.
Figure 3:
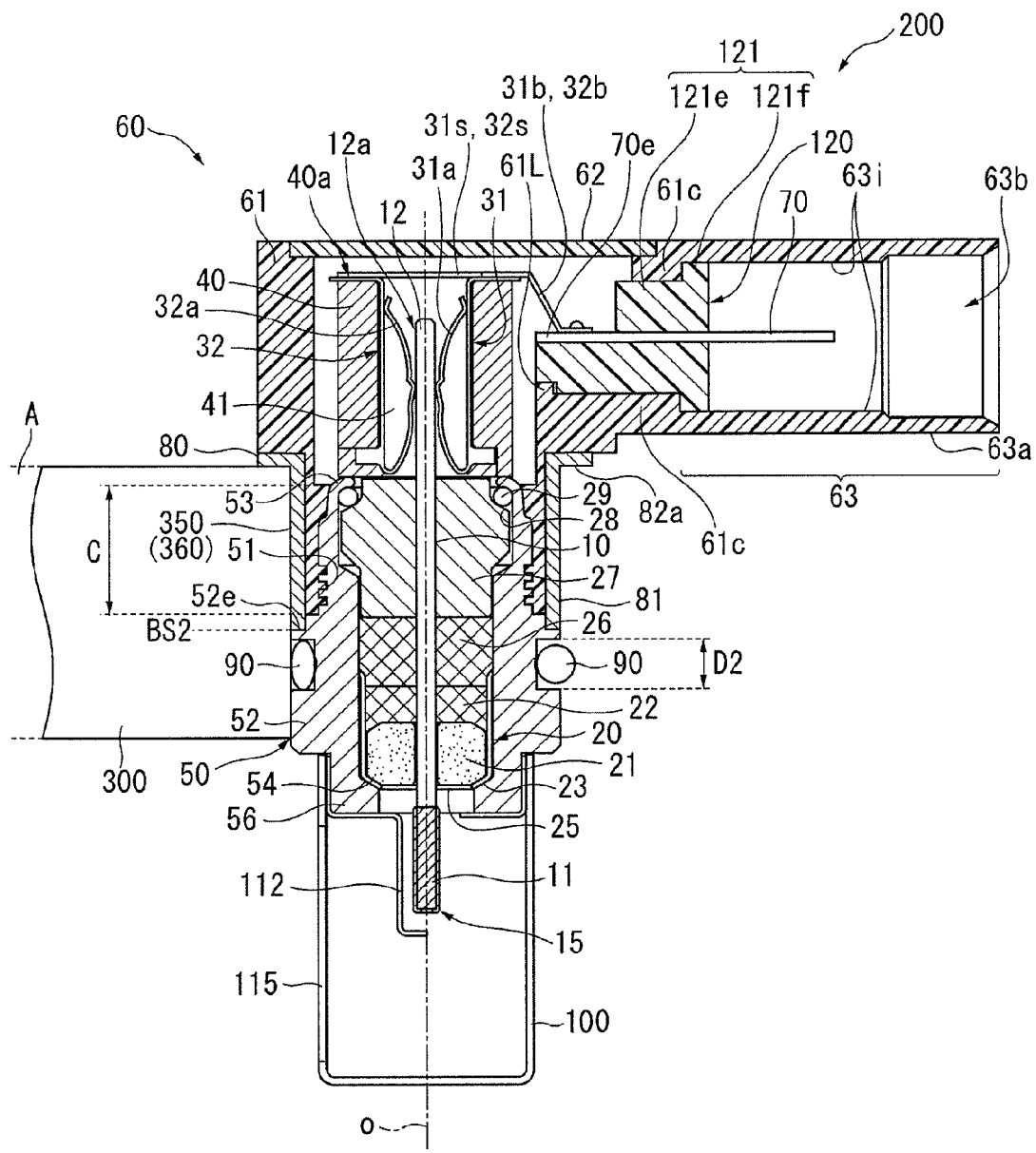
FIG. 3 is a sectional view taken along line III-III of FIG. 2.

FIG. 1 is a perspective view showing an example of the schematic configuration of an element assembly 150 held within a gas sensor 200 according to a first embodiment of a first aspect of the present invention; FIG. 2 is a perspective view of the gas sensor 200 according to the first embodiment; and FIG. 3 is a sectional view taken along line III-III of FIG. 2.

In FIG. 1, the direction of an axis O (represented by the dash-dot line) of a gas sensor element 10 coincides with the vertical direction. In the following description, a side toward a rear end portion 12 is referred to as the rear side of the gas sensor element 10 (and of the gas sensor), and an opposite side toward a detection portion of the gas sensor element 10 is referred to as the front side of the gas sensor element 10 (and of the gas sensor). A direction perpendicular to the direction of the axis O is referred to as a "radial direction" as appropriate.

As shown in FIG. 2, the gas sensor 200 includes the element assembly 150 (including the gas sensor element 10); a cover 60 formed of resin and joined to a housing 50 (see FIG. 1) of the element assembly 150; a heat sink member 80 made of metal and radially surrounding a front end portion of the cover 60; a separator 40 made of ceramic and accommodated within the cover 60; and connection terminals 31 and 32 attached to the separator 40. In the present first embodiment, the cover 60 is composed of a cover body 61 fixed to the housing 50 by insert molding, and a lid 62 fitted to the cover body 61 from the rear side for closing the internal space of the cover body 61. A seal member (O ring) 90 is externally fitted into a groove circumferentially formed in a front end portion of the housing 50.

Notably, the cover 60 (the cover body 61 and the lid 62) corresponds to the "cover" of the invention.

The gas sensor element 10 is a publicly known substantially rectangular columnar laminate which extends in the direction of the axis O and in which a detection element for detecting an oxygen concentration and a heater for promptly activating the detection element by application of heat are bonded together. The detection element is configured such that a solid electrolyte member which contains zirconia as a main component, and a pair of electrodes which contain platinum as a main component, are laminated together via an insulation layer having a hollow measuring chamber formed therein. More specifically, the detection element has an oxygen pump cell and an oxygen-concentration-measuring cell. The oxygen pump cell is configured as follows: one of a pair of electrodes formed on the respective opposite sides of a solid electrolyte member is exposed outward, whereas the other electrode is exposed to the measuring chamber. The oxygen-concentration-measuring cell is configured as follows: one of a pair of electrodes formed on the respective opposite sides of a solid electrolyte member is exposed to the measuring chamber, whereas the other electrode is exposed to a reference gas chamber. Current to be applied between the paired electrodes of the oxygen pump cell is controlled in such a manner that an output voltage of the oxygen-concentration-measuring cell assumes a predetermined value, thereby pumping oxygen out from the measuring chamber or pumping oxygen into the measuring chamber from outside.

In the oxygen pump cell, the pair of electrodes and a portion of the solid electrolyte member sandwiched between the electrodes collectively serve as a detection portion 11 (FIG. 3) in which current flows according to the concentration of oxygen. A rear end portion 12 of the gas sensor element 10 has five electrode pads 12a (FIG. 1 shows two of them formed on a second surface 10b of the gas sensor element 10, and the remaining three are formed on a first surface 10a not shown in FIG. 1) formed thereon for leading output signals out from the detection element and for supplying power to the heater.

As shown in FIG. 3, a closed-bottomed tubular metal cup 20 is disposed slightly frontward of the axial center of the gas sensor element 10 in such a manner that the gas sensor element 10 is inserted through the interior of the metal cup 20 with the detection portion 11 projecting from an opening 25 formed in the bottom of the metal cup 20. The metal cup 20 is a member for holding the gas sensor element 10 in the housing 50. A front-end peripheral portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such a manner that the gas sensor element 10 is inserted through the ceramic ring 21 and through the talc ring 22. The talc ring 22 is crushed within the metal cup 20 so as to tightly fill an associated space, thereby holding the gas sensor element 10 in position in the metal cup 20.

An assembly of the metal cup 20 and the gas sensor element 10 is radially surrounded by and held by the housing 50 made of metal, the housing 50 being inserted into a sensor-mounting hole 350 of an mounting body 300. The housing 50 is formed from stainless steel such as SUS430. The housing 50 has a large-diameter portion 52 having the largest outside diameter and located substantially at the central position with respect to the direction of the axis O of the housing 50. The housing 50 also has a stepped portion 52e formed rearward of the rear end of the large-diameter portion 52 in such a manner as to be reduced in diameter in two steps. Furthermore, the housing 50 has an array of grooves 51 located rearward of the stepped portion 52e, formed on the outer circumferential surface thereof, and arranged in the direction of the axis O. The array of grooves 51 enhances adhesion between the housing 50 and the cover (as described below) made of resin by a wedge effect. The housing 50 further has a crimp portion 53 located rearward of the array of grooves 51. The crimp portion 53 is adapted to hold the gas sensor element 10 in the housing 50 through crimping.

The housing 50 has a groove D2 formed in a circumferentially continuous manner on the outer surface of the large-diameter portion 52. A seal member (O ring) 90 is externally fitted into the groove D2.

The housing 50 further has a front-end engagement portion 56 located frontward of the large-diameter portion 52. An outer protector 100, as described below, is engaged with the front-end engagement portion 56. The housing 50 has an inner stepped portion 54 on its inner circumferential surface at a position substantially corresponding to the front-end engagement portion 56. The front-end peripheral portion 23 of the metal cup 20, which holds the gas sensor element 10, is engaged with the inner stepped portion 54. Furthermore, a talc ring 26 is placed into the housing 50 along the inner circumference of the housing 50 toward the rear end of the metal cup 20 in such a state that the gas sensor element 10 is inserted through the talc ring 26. A tubular sleeve 27 is fitted into the housing 50 in such a manner as to press the talc ring 26 from the rear end of the talc ring 26. The sleeve 27 has a step-like shoulder portion 28 formed on the outer circumferential surface of a rear end portion of the sleeve 27. An annular crimp packing 29 is disposed on the shoulder portion 28.

The crimp portion 53 of the housing 50 is crimped in such a manner as to press the shoulder portion 28 of the sleeve 27 frontward via the crimp packing 29. By forming the crimp portion 53, the talc ring 26 pressed through the sleeve 27 is crushed within the housing 50, thereby tightly filling an associated space. By means of the talc ring 26 and the talc ring 22, which is previously placed in the metal cup 20, the metal cup 20 and the gas sensor element 10 are held in position in the housing 50 in a gastight manner.

Referring back to FIG. 2, the heat sink member 80 integrally has a cylindrical heat sink casing portion 81 and two semicircular flange portions 82 extending radially outward from the rear end of the heat sink casing portion 81. Each of the flange portions 82 has a through-hole 83. Screws are inserted through the respective through-holes 83 and screwed into respective threaded holes formed in the mounting body 300 (e.g., an intake system of an internal combustion engine) (see FIG. 3), whereby the gas sensor 200 can be mounted to the mounting body 300. Frontward-oriented surfaces (back surfaces) 82a of the flange portions 82 are flush with each other and come into close contact with the outer surface of the mounting body 300 (see FIG. 3).

The outside diameter of the heat sink casing portion 81 is equal to the outside diameter of the large-diameter portion 52 of the housing 50. The inside diameter of the heat sink casing portion 81 is substantially equal to the outside diameter of the wall surface of an outer stepped subportion of the stepped portion 52e. Thus, when a rear portion of the housing 50 is covered with the heat sink casing portion 81, the front end of the heat sink casing portion 81 is closely fitted to the outer stepped subportion of the stepped portion 52e, and the outer surface of the heat sink casing portion 81 and the outer surface of the large-diameter portion 52 are flush with each other. Furthermore, a clearance corresponding to the radial dimension of an inner stepped subportion of the stepped portion 52e is formed between the inner surface of the heat sink member 80 and a portion of the housing 50 extending from the array of grooves 51 to the crimp portion 53. In this condition, a mating surface between the stepped portion 52e and the front end of the heat sink casing portion 81 is subjected to full-circle laser welding or the like, whereby the heat sink member 80 radially surrounds a rear portion of the housing 50.

The heat sink member 80 can be formed from, for example, aluminum, an aluminum alloy, or stainless steel. The heat sink member 80 may be higher or lower in thermal conductivity than the housing 50. However, preferably, the heat sink member 80 has a higher thermal conductivity than that of the cover 60, as described below.

Next, the cover 60 will be described with reference to FIGS. 2 and 3. In the present embodiment, the cover body 61 is formed from a NYLON (registered trademark) resin, which is a resin of good moldability, by insert molding into the above-mentioned clearance between the housing 50 and the heat sink member 80. Particularly, by means of the cover body 61 and the housing 50 being joined together via the array of grooves 51, which collectively have a large surface area, by virtue of the wedge effect, adhesion and sealing performance between the cover body 61 and the housing 50 are improved.

The front end of the cover body 61 is in contact with the inner stepped subportion of the stepped portion 52e of the housing 50. The outer stepped subportion of the stepped portion 52e of the housing 50 and the front end of the heat sink casing portion 81 define a joint interface BS2 therebetween. A region extending from the inner stepped subportion of the stepped portion 52e to the vicinity of the crimp portion 53 serves as a joint portion C between the cover body 61 and the housing 50. In the example of FIG. 3, the entire joint portion C is disposed axially inward (frontward) of the outer surface of the mounting body 300 around the sensor-mounting hole 350 (i.e., a mounting surface A, as described below). The heat sink member 80 (the heat sink casing portion 81 thereof) radially surrounds the contact portion (the joint portion C) fully. The joint interface BS2 is located frontward of the front end of the joint portion C with respect to the direction of the axis O.

On the rear side of the crimp portion 53, the cover body 61 has a semicylindrical portion 61a having a diameter greater than that of the large-diameter portion 52 of the housing 50 and oriented toward the same side as that toward which a gas introduction hole 115 is formed in the outer protector 100. Also, two wall portions 61b extend in parallel from the respective ends of the semicylindrical portion 61a toward a side opposite the gas introduction hole 115. Upper and lower engagement walls 61c project from upper and lower portions, respectively, of the ends of the two wall portions 61b perpendicularly to the surfaces of the wall portions 61b. A connector terminal member 120 projects into the internal space of the cover body 61 from a gap between the upper and lower engagement walls 61c. Thus, the semicylindrical portion 61a, the two wall portions 61b, and the connector terminal member 120 (more specifically, an insulator 121) surround the rear end portion 12 of the gas sensor element 10. The respective rear ends of the semicylindrical portion 61a, the two wall portions 61b, and the engagement walls 61c are slightly higher than the rear end portion 12 of the gas sensor element 10. Accordingly, the rear end portion 12 (also, the separator 40 and connector terminals 70, as described below) is accommodated within the internal space of the cover body 61.

Furthermore, the cover body 61 integrally has a rectangular male connector portion 63 extending outward in a radial direction (a direction perpendicular to the direction of the axis O) of the gas sensor 200 and having an opening 63b on a side opposite the gas introduction hole 115, as described below. The connector portion 63 is configured such that a connector wall 63a which defines the opening 63b surrounds the connector terminal member 120 inserted into the connector portion 63 and is integrally connected to the engagement walls 61c. The connector terminal member 120 projects into the internal space of the cover from the engagement walls 61c. Furthermore, one ends 70e (see FIG. 6) of the connector terminals 70 are exposed.

The connector portion 63 may extend in a direction (e.g., the direction of the axis O) other than a radial direction of the gas sensor 200. However, in view of the necessity to shorten the length of outward projection of the gas sensor 200 from an intake pipe of an internal combustion engine, or the like when the gas sensor 200 is mounted to the intake pipe or the like, preferably, the connector portion 63 extends in a radial direction of the gas sensor 200. This enables provision of a clearance between the hood and the engine parts of a vehicle having an internal combustion engine in order to mitigate impact imposed by a colliding object with which the vehicle collides.

The connector portion 63 allows a mating external connector (in the present embodiment, a female connector) to be inserted thereinto and removed therefrom. The connector terminals (in the present embodiment, five pieces) 70 are integrally insert-molded to the insulator 121 (see FIG. 6) in such a manner as to be spaced apart from one another, thereby configuring the connector terminal member 120. The insulator 121 is made of resin; however, for example, rubber or any other high polymer material may be used to form the insulator 121 so long as the material is adaptable to insert molding.

As shown in FIG. 3, the connector terminal member 120 is inserted, for attachment, into the opening 63b of the connector portion 63 from outside in a radial direction (the direction of the arrow of FIG. 5). Specifically, the insulator 121 of the connector terminal member 120 has a terminal member body 121e and a flange portion 121f; the terminal member body 121e holds the connector terminals 70 in such a manner as to insulate the connector terminals 70 from one another while one ends 70e of the connector terminals 70 are exposed on the upper surface thereof; and the flange portion 121f expands from the terminal member body 121e on a side toward the other ends of the connector terminals 70 (see FIG. 6). The connector terminals 70 on the side toward the other ends thereof project from the flange portion 121f while being spaced apart from one another, thereby constituting male pins.

Meanwhile, the engagement walls 61c form respective stepped portions projecting from the upper and lower sides (the rear side and the front side) of an inner surface 63i of the opening 63b toward the vertical center of the opening 63b. The outline of the flange portion 121f is slightly smaller in size than the circumferential profile of the inner surface 63i of the opening 63b. When the connector terminal member 120 is inserted into the opening 63b, the flange portion 121f traces the inner surface 63i; thus, the connector terminal member 120 is reliably positioned. When the flange portion 121f comes into contact with the upper and lower engagement walls 61c, further insertion of the connector terminal member 120 is prevented. Thus, the attachment of the connector terminal member 120 is completed in a condition in which only the terminal member body 121e (and the one ends 70e of the connector terminals 70 exposed on the upper surface thereof) projects into the internal space of the cover from the engagement walls 61c.

When the flange portion 121f comes into contact with the upper and lower engagement walls 61c, a recessed engagement portion 121L (see FIG. 6) formed at an end of the terminal member body 121e is engaged with a hooked lock portion 61L projecting from the lower engagement wall 61c, whereby the connector terminal member 120 is fixed to the connector portion 63.

In this manner, by means of preparing, as a separate component, the connector terminal member 120 in which a plurality of the connector terminals 70 are integrated with the insulator 121, and connecting afterward the connector terminal member 120 to the connection terminals 31 and 32, there is no need to press-fit the connection terminals 31 and 32 (or the connector terminals 70) afterward one by one to the cover 60 (the connector portion 63), thereby improving productivity. Also, since there is no need to insert-mold the connection terminals 31 and 32 to the cover 60 (the connector portion 63), a mold for the cover does not need to have high dimensional accuracy, and the structure of the mold becomes simple, thereby reducing manufacturing costs. As described below, even when insert molding is employed in manufacturing the connector terminal member 120, required dimensional accuracy is lower than in the case of a mold for the cover. This is because the connector terminal member 120 is simple in shape in contrast to the connector portion 63 having a tubular portion.

Furthermore, by utilizing the opening 63b of the connector portion 63 through which an external connector is inserted and removed, the connector terminal member 120 is inserted through the opening 63b in the insertion/removal direction of the external connector, whereby the cover 60 does not need to have another hole for inserting the connector terminal member 120. Thus, the structure of the cover 60 (the connector portion 63) becomes simple, and the number of components is reduced.

Meanwhile, the gas sensor element 10 is disposed as follows: the rear end portion 12 projects rearward of the rear end (the crimp portion 53) of the housing 50 and is covered with a tubular separator 40 made of an insulating ceramic. A reception hole 41 of the separator 40 accommodates the electrode pads 12a provided on the rear end portion 12 of the gas sensor element 10. The connection terminals 31 and 32 disposed within the reception hole 41 are electrically connected to the corresponding electrode pads 12a. Ends of the connection terminals 31 and 32 (external-circuit connection terminal ends, as described below) disposed externally of the separator 40 extend in a radial direction and are electrically connected to the corresponding one ends 70e of the connector terminals 70.

As described above, the electrode pads 12a of the gas sensor element 10 and the connector terminals 70 are electrically connected via the connection terminals 31 and 32. In this condition, the lid 62 is fitted to the cover body 61, and then the two members are joined together (through, for example, fusion). By this procedure, the separator 40 is covered with the cover 60, thereby yielding the gas sensor 200.

The separator 40 is not an essential component of the present invention. Without use of the separator, the connection terminals 31 and 32 can be disposed in such a manner as to be spaced apart (insulated) from one another. However, by use of the insulating separator 40 extending in the direction of the axis O and having a reception hole into which the connection terminals 31 and 32 are inserted, the connection terminals 31 and 32 can be held while being reliably spaced apart (insulated) from one another. The separator may be a tubular member which covers the reception hole fully along the circumferential direction, or a tubular member having a cutout through which a portion of the reception hole is exposed to the exterior of the separator.

Meanwhile, the detection portion 11 of the gas sensor element 10 is coated with a porous protection layer 15 so as to protect externally exposed electrodes of the detection portion 11 from poisoning and water adhesion caused by intake gas or the like. The outer protector 100 is fitted to and laser-welded to the front-end engagement portion 56 of the housing 50, thereby being fixed in position. The outer protector 100 protects the detection portion 11 accommodated therein.

Meanwhile, the outer protector 100 has the gas introduction hole 115 formed therein and adapted to expose the detection portion 11 of the gas sensor element 10 to gas. The gas introduction hole 115 assumes the form of a slit extending in the axial direction. By employing the gas introduction hole 115 in the form of a slit, gas contained in the outer protector 100 is promptly renewed, thereby restraining a deterioration in the detection accuracy of the gas sensor element 10. In the first embodiment, the gas introduction hole 115 has a width of 1.0 mm. In this manner, when the gas introduction hole 115 has a width of 0.5 mm or greater, gas contained in the outer protector 100 is promptly renewed, whereby a deterioration in gas detection accuracy can be prevented.

When the gas sensor 200 is mounted to an intake system of an internal combustion engine, orienting the gas introduction hole 115 toward the downstream direction of the intake system can restrain the generation of cracking in the gas sensor element 10 and can restrain a deterioration in the detection accuracy of the gas sensor 200.

Thus, it is good practice to fix the heat sink member 80 to a rear portion of the housing 50 while the extending direction of the flange portions 82 and the orientation of the gas introduction hole 115 are adjusted in such a manner that, when the gas sensor 200 is mounted, the gas introduction hole 115 is oriented toward the downstream direction of the intake system.

Furthermore, an inner protector 112 is disposed within the outer protector 100 between the detection portion 11 and the gas introduction hole 115 so as to restrain direct exposure of the detection portion 11 to gas which is introduced into the outer protector 100 through the gas introduction hole 115. Thus, adhesion of water and oil contained in gas to the gas sensor element 10 and the generation of cracking in the gas sensor element 10 can be restrained. Also, adhesion of soot contained in gas to the gas sensor element 10 can be restrained. Therefore, deterioration in the detection accuracy of the gas sensor 200 can be restrained.

Next, the configuration of the electrically conductive members 31, 32, and 70 will be described with reference to FIGS. 3 and 4.

The connection terminals 31 and 32 are formed as follows: strip-like electrically conductive members (metal pieces) are stamped out by use of a press or the like, and the conductive members thus obtained are bent into a predetermined shape. The connection terminals 31 and 32 integrally have element connection-terminal portions 31*a* and 32*a* disposed within the reception hole 41 of the separator 40 and connected to the corresponding electrode pads 12*a*, and external-circuit connection-terminal portions 31*b* and 32*b* for connecting the element connection-terminal portions 31*a* and 32*a* to the connector terminals 70.

The element connection-terminal portions 31*a* and 32*a* have lead subportions 31*t* and 32*t* extending along the wall surface of the reception hole 41, and contact subportions 31*r* and 32*r* bent at the front ends of the lead subportions 31*t* and 32*t* and bulging, for providing elastic force, toward a center plane which contains the axis of the separator 40. When the rear end portion 12 of the gas sensor element 10 is inserted into the reception hole 41 of the separator 40, the element connection-terminal portions 31*a* and 32*a* (the contact subportions 31*r* and 32*r*) come into sliding contact with the corresponding electrode pads 12*a*, and the elastic force of the element connection-terminal portions 31*a* and 32*a* increases the pressure of contact with the electrode pads 12*a*, thereby ensuring reliable electrical connection.

The external-circuit connection-terminal portions 31*b* and 32*b* will next be described in detail with reference to FIG. 4. FIG. 4 is a perspective view showing the configuration of the connection terminals of the gas sensor according to the first embodiment.

Each of the external-circuit connection-terminal portions 31*b* integrally has a horizontal subportion 31*s* extending from the lead subportion 31*t* via a first bent subportion 31*e* and extending in a radial direction along an upper surface 40*a* of the separator 40; a first terminal subportion 31*b*1 extending from the horizontal subportion 31*s* via a second bent subportion 31*f* in an obliquely extending manner so as to extend toward the axial center of the separator 40 and radially outward; and a second terminal subportion 31*b*2 extending from the first terminal subportion 31*b*1 horizontally and radially outward via a third bent subportion 31*g*.

Each of the external-circuit connection-terminal portions 32*b* integrally has a horizontal subportion 32*s* extending from the lead subportion 32*t* via a first bent subportion 32*e* and extending in a radial direction along the upper surface 40*a* of the separator 40; a first terminal subportion 32*b*1 extending from the horizontal subportion 32*s* via a second bent subportion 32*f* in an obliquely extending manner so as to extend toward the axial center height of the separator 40 and radially outward; and a second terminal subportion 32*b*2 extending from the first terminal subportion 32*b*1 horizontally and radially outward via a third bent subportion 32*g*.

The first terminal subportions 31*b*1 and the first terminal subportions 32*b*1 have the same angle of inclination. The second terminal subportions 31*b*2 and the second terminal subportions 32*b*2 are arrayed in a row.

Figure 4:
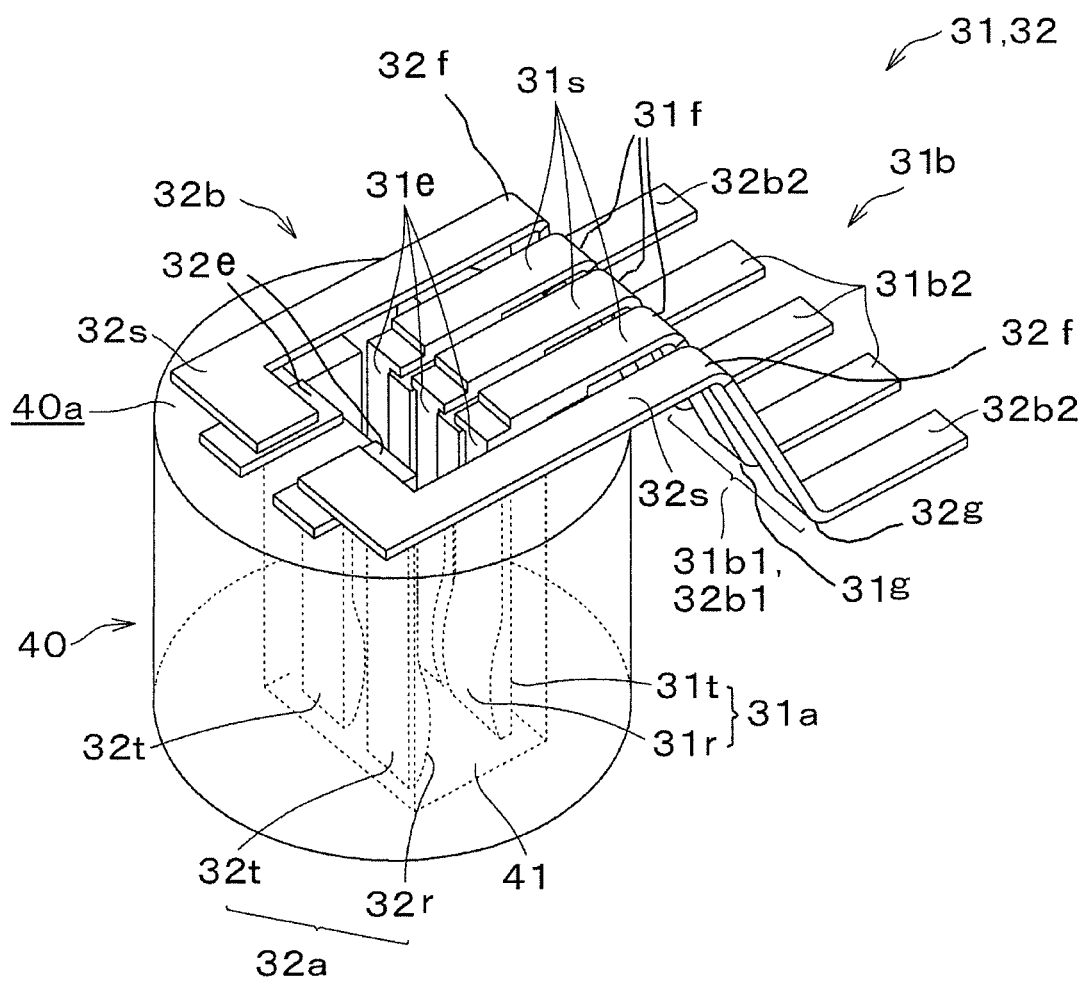
FIG. 4 is a perspective view showing the configuration of connection terminals of the gas sensor according to the first embodiment.

The horizontal subportions 31*s* of the connection terminals 31 extend straight from the reception hole 41 of the separator 40 toward the far side of FIG. 4. By contrast, in order to avoid contact with the horizontal subportions 31*s*, the horizontal subportions 32*s* of the connection terminals 32 extend on a side toward the circumference of the reception hole 41 and extend straight from outside the three horizontal subportions 31*s* toward the far side of FIG. 4.

In this manner, the connection terminals 31 and 32 extend in a radial direction from the rearward-oriented upper surface 40*a* of the separator 40; i.e., the connection terminals 31 and 32 and lead wires, etc., to be connected to the connection terminals 31 and 32 do not project rearward from the rearward-oriented upper surface 40*a* of the separator 40. Thus, the height of the gas sensor 200 along the direction of the axis O is lowered accordingly, whereby the length of projection of the gas sensor 200 from a mounting body can be shortened, as measured when the gas sensor 200 is mounted to the mounting body.

Since the external-circuit connection-terminal portions 31*b* and 32*b* are bent toward the axial center of the separator 40, the axial height of the connector terminals 70 connected to the bent ends of the external-circuit connection-terminal portions 31*b* and 32*b* can be lowered frontward. The outline of the connector portion 63 is such that it projects rearward and frontward with respect to the connector terminals 70 so as to allow a mating connector to be radially fitted into and removed from the connector portion 63. However, by lowering the positional height of the connector terminals 70, the positional height of the connector portion 63 is lowered accordingly. Thus, the height of the gas sensor 200 as measured along the direction of the axis O is lowered accordingly, whereby the length of projection of the gas sensor 200 from a mounting body can be shortened, as measured when the gas sensor 200 is mounted to the mounting body.

The thus-configured gas sensor 200 can be mounted to the mounting body 300 in the following manner.

First, the seal member 90 attached to the housing 50 has an outside diameter that is greater than that of the large-diameter portion 52, and the mounting body 300; i.e., a body to which the gas sensor is to be mounted, has the sensor-mounting hole 350, which has a slightly greater diameter than that of the large-diameter portion 52. Thus, when the gas sensor 200 is inserted, for mounting, from its front end into the sensor-mounting hole 350, the seal member 90 is squeezed by an inner wall 360 of the sensor-mounting hole 350, thereby providing a seal between the housing 50 and the mounting body 300.

As shown in FIG. 3, the frontward-oriented surfaces (back surfaces) 82*a* of the flange portions 82 are in contact with the outer surface (the mounting surface A) of the mounting body 300. Furthermore, screws are inserted through the respective through-holes 83 of the flange portions 82 and threadingly engaged with respective threaded holes formed in the mounting body 300, whereby the gas sensor 200 is mounted to the mounting body 300.

In this manner, the joint portion C between the housing 50 and the cover 60 (the cover body 61) is disposed axially inward (frontward) of the outer surface of the mounting body 300 around the sensor-mounting hole 350 (i.e., the mounting surface A). Thus, the length of outward projection, from the mounting body 300, of the gas sensor 200 including the cover 60 can be shortened. Notably, a portion of the housing 50 may be located axially outward of the outer surface of the mounting body 300 around the sensor-mounting hole 350.

The heat sink member 80 (the heat sink casing portion 81 thereof) radially surrounds the joint portion C. Also, while the front end of the heat sink casing portion 81 is in contact with the housing 50 at a position located frontward of the joint portion C, the flange portions 82 integral with the heat sink casing portion 81 are exposed outward (rearward) of the outer surface of the mounting body 300 around the sensor-mounting hole 350 (i.e., the mounting surface A). Thus, heat of the housing 50, whose temperature becomes high, is radiated to the mounting body 300, the atmosphere, etc., through the heat sink member 80 (particularly through the flange portions 82). By virtue of this, heat does not stagnate in the joint portion C, which is a portion of the cover 60 subjected to the highest thermal load, thereby reducing thermal influence on the cover 60 (the cover body 61).

Preferably, the position where the heat sink member 80 and the housing 50 are in contact with each other coincides with the axial position of the front end of the joint portion C or is located frontward of the front end of the joint portion C. However, in order to reduce thermal influence on the cover 60, the more frontward the contact position is located as viewed in the axial direction, the better. The heat sink member 80 surrounds (covers) the joint portion C as viewed from radial directions. However, the heat sink member 80 may cover the joint portion C while leaving uncovered portions as viewed along the circumferential direction, instead of covering fully along the circumferential direction.

Particularly, in the case where the mounting body 300 is made of resin, even though the heat sink casing portion 81 is in contact with the inner wall 360 of the sensor-mounting hole 350, heat radiation through the inner wall 360 is less effective. Therefore, it is effective to expose the flange portions 82 outward of the mounting surface A.

Furthermore, outward radiation of heat of the housing 50 can reduce thermal influence on the O ring 90 attached to the housing 50.

Examples of the mounting body 300; i.e., examples of a body to which the gas sensor 200 is to be mounted, include various internal combustion engines; particularly, intake systems of internal combustion engines of vehicles, such as automobiles. The intake system is an intake path extending between an intake to an intake port of an internal combustion engine; for example, an intake pipe or an intake manifold, which branches off from the intake pipe and is connected to the intake port of the internal combustion engine. Intake gas includes fresh air (fresh air which does not contain exhaust gas) and a mixed gas of fresh air and exhaust gas refluxed (recirculated) to the intake system.

The gas sensor element 10 of the present embodiment is a so-called full range air/fuel ratio sensor. However, in addition to the full range air/fuel ratio sensor, an oxygen sensor ($\lambda$ sensor) and an $NO_x$ sensor can be used.

As compared with control of an internal combustion engine on the basis of the concentration of a particular gas contained in exhaust detected by a gas sensor provided in an exhaust system, control of the internal combustion engine on the basis of the concentration of a particular gas detected by a gas sensor provided in an intake system exhibits higher accuracy of control of the internal combustion engine. This is because control on the basis of the concentration of a particular gas contained in exhaust is feedback control, whereas control on the basis of the concentration of a particular gas in the intake system is precombustion control. Needless to say, an internal combustion engine can be controlled with higher accuracy by means of control based on the concentration of a particular gas detected at both of the intake and exhaust sides.

Next, an example method of manufacturing the gas sensor 200 according to the first embodiment of the present invention will be described with reference to FIGS. 5A to 5F.

Figure 5A:
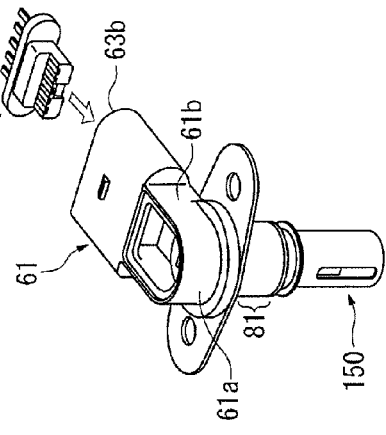
FIGS. 5A to 5F are process drawings showing an example method for manufacturing the gas sensor according to the first embodiment.
Figure 5B:
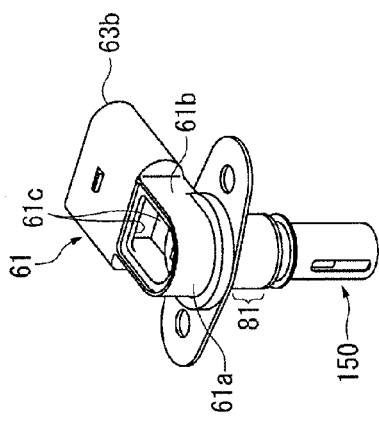
Figure 5C:
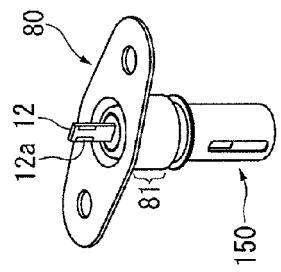

First, the front end of the heat sink casing portion 81 of the heat sink member 80 is fitted to the stepped portion 52e (see FIG. 3) of the housing 50 of the element assembly 150 fabricated by a publicly known method. The associated mating surface is subjected to full-circle laser welding, thereby connecting the heat sink member 80 to a rear portion of the housing 50 (FIG. 5A). Next, the cover body 61 is formed around the rear end of the heat sink member 80 through insert molding (FIG. 5B). Next, the connector terminal member 120 is inserted into the opening 63b of the connector portion 63 from the outside (FIG. 5C) in a radial direction (the direction of the arrow of FIG. 5C). At this time, when the flange portion 121f (see FIGS. 3 and 6) comes into contact with the engagement walls 61c, further insertion of the connector terminal member 120 is prevented, thereby positioning the connector terminal member 120. Thus, the connector terminal member 120 is provided in such a manner that only the terminal member body 121e (and the one ends 70e of the connector terminals 70) projects into the internal space of the cover 61.

Figure 5D:
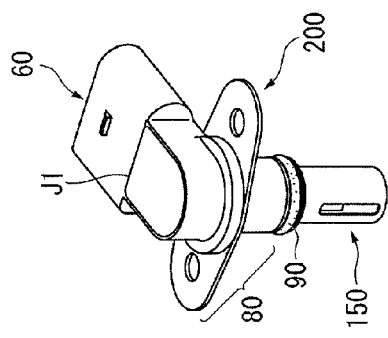

Next, the separator 40 to which the connection terminals 31 and 32 are attached beforehand is fitted to the rear end portion 12 of the gas sensor element 10 disposed within the cover body 61, thereby connecting the connection terminals 31 and 32 to the corresponding electrode pads 12a and to the corresponding connector terminals 70 (FIG. 5D). Also, electrical connection is established as appropriate between the connection terminals 31 and 32 and the corresponding connector terminals 70 by spot welding or the like. If there is a case where the connector terminal member 120 is extracted (removed) from the opening 63b of the connector portion after insertion thereof, preferably, the connection terminals 31 and 32 and the connector terminals 70 are connected in a removable manner (e.g., rod-like connection portions of the connector terminals 70 are tightly fitted into respective tubular connection portions of the connection terminals 31 and 32).

Figure 5E:
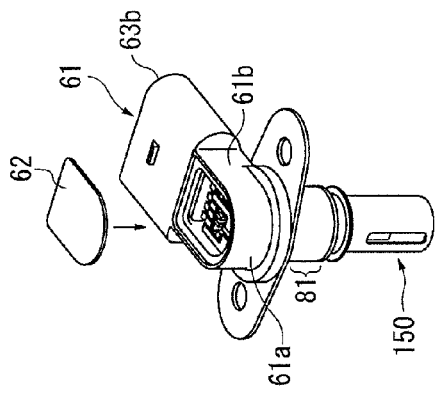
Figure 5F:
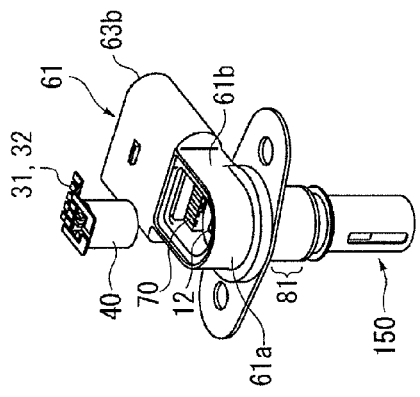

Then, the lid 62 is fitted to the opening of the cover body 61 (FIG. 5E). The lid 62 and the cover body 61 are joined (e.g., fused) together along a joint J1, thereby providing a seal. The cover 60 is thus formed. The O ring 90 is externally fitted into the groove D2 (not shown) of the large-diameter portion 52 (not shown), thereby yielding the gas sensor 200 (FIG. 5F).

Next, an example method for manufacturing the connector terminal member will be described with reference to FIGS. 6A to 6C. The connector terminals 70 must be prepared in a plurality of pieces according to the number of mating terminals; i.e., the number of the connection terminals 31 and 32. When the insulator 121 is to be insert-molded around the connector terminals 70, employing a step of arranging a plurality of the connector terminals 70 at predetermined intervals within a mold for insert-molding may reduce workability.

Figure 6A:
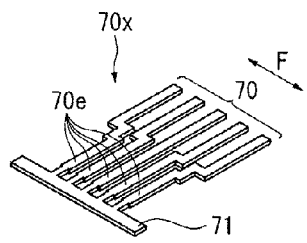
FIGS. 6A to 6C are process drawings showing an example method for manufacturing a connector terminal member 120.

Thus, in the example of FIG. 6, a connector terminal cluster 70x in which a plurality of the connector terminals 70 are integrally connected to a joint 71 at their one ends 70e is prepared beforehand. The single connector terminal cluster 70x is disposed within a mold for insert molding (FIG. 6A). The connector terminal cluster 70x can be integrally formed through, for example, blanking. The connector terminal cluster 70x holds the connector terminals 70 while the connector terminals 70 are spaced apart from one another at predetermined intervals. This eliminates the need to arrange a plurality of the connector terminals 70 at predetermined intervals within a mold for insert molding, thereby improving productivity. Also, since the joint 71 holds the connector terminals 70 at predetermined intervals, the accuracy of the connector terminal member 120 is improved.

Figure 6B:
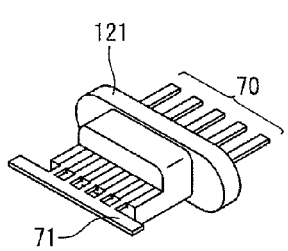

Then, the connector terminal cluster 70x is insert-molded to the insulator 121, thereby integrally molding the insulator 121 with the connector terminal cluster 70x (FIG. 6B). At this time, molding is performed in such a manner that the joint 71 is disposed externally of the insulator 121. The exposed connector 71 is cut off from the connector terminals 70, thereby yielding the connector terminal member 120 (FIG. 6C).

Figure 6C:
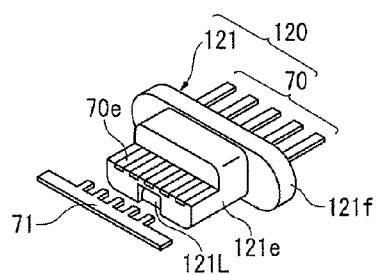

In the example shown in FIGS. 6A to 6C, the connector terminals 70 are spread on a side opposite the one ends 70e in a radial direction F of the gas sensor element 10 (see FIG.

6A). By virtue of this, while intervals of the connector terminals 70 are narrowed on a side toward the one ends 70e to be connected to the connection terminals 31 and 32 so as to allow the gas sensor 200 to be reduced in size, intervals of the connector terminals 70 on a side opposite the one ends 70e are widened so as to stabilize connection to an external connector.

When the connector terminals 70 are bent as mentioned above, difficulty is encountered in press-fitting the connector terminals 70 to the insulator 121 without employing insert molding. However, by means of the insulator 121 being molded through insert molding, the connector terminals 70 and the insulator 121 can be integrated with each other to form the connector terminal member 120, regardless of the shape of the connector terminals 70.

Also, the connector terminals 70 may be bent in the direction of the axis O. In this case, the center of the connector can be lowered, whereby the length of projection of the gas sensor 200 can be shortened.

The invention has been described by reference to the above embodiment. However, the invention should not be construed as being limited thereto. It should further be apparent to those skilled in the art that various changes in form and detail of the invention as shown and described above may be made. It is intended that such changes be included within the spirit and scope of the claims appended hereto.

Figure 7:
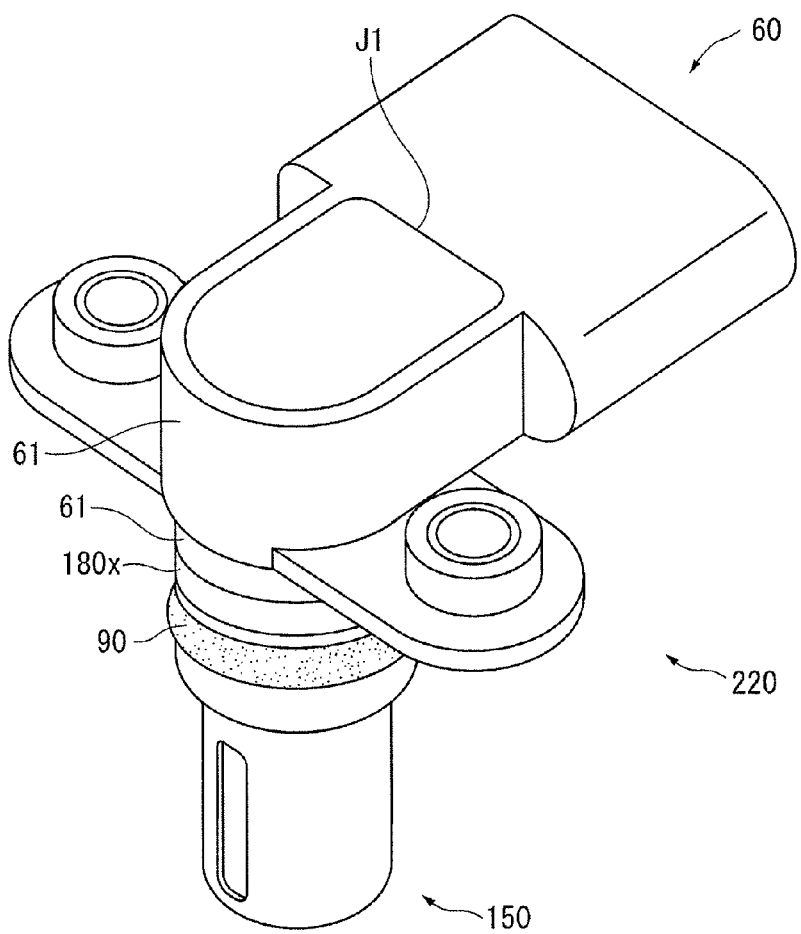
FIG. 7 is a perspective view showing another configuration of the gas sensor.

For example, according to the above-described first embodiment, the heat sink member 80 (the heat sink casing portion 81 thereof) externally surrounds the contact portion fully. However, the following configuration may be employed. As shown in FIG. 7, while a heat sink member 180x is disposed only at a front subportion of the joint portion C, the cover body 61 is insert-molded, whereby a portion of the cover body 61 extends (is exposed) coaxially from the rear end of the heat sink member 180x. Thermal load is imposed on an exposed portion of the cover body 61; i.e., on an exposed subportion of the joint portion C. However, when, for example, the working condition of the gas sensor is not severe such that a working temperature condition allows the joint portion C to be partially exposed, the modified embodiment of FIG. 7 can be employed.

The heat sink member is not an essential component of the present invention. While the connector portion and the cover are made of resin, the heat sink member may be eliminated according to a working condition of the gas sensor. In this case, the cover is provided on the rear side of the housing. Also, the connector portion and the cover may be made of metal. When the connector portion and the cover are made of metal, heat resistance and thermal conductivity are improved such that the heat sink member may be eliminated. In this case, the insulator of the connector terminal member insulates the connector portion and the connector terminals from each other.

In the first embodiment described above, the cover 60 is joined to the housing 50 through insert molding. However, the present invention is not limited thereto. The cover 60 may be joined to the housing 50 through, for example, fitting, such as press fitting or loose fitting, crimping, welding, or fusing.

In addition to the O ring, a sheet packing can be used as the seal member 90.

In the embodiment described above, the cover 60 is molded from a NYLON resin. However, no problem arises even when the cover 60 is molded from another publicly known high polymer material.

The application claims priority from Japanese Patent Application No. 2010-198034 filed Sep. 3, 2010, incorporated herein by reference in its entirety.

What is claimed is:

1. A gas sensor comprising:
a gas sensor element extending in an axial direction, having a detection portion provided at a front end thereof for detecting a particular gas component in a gas to be measured, and having electrode pads provided at a rear end thereof;
connection terminals electrically connected to the respective electrode pads; and
a cover covering the rear end of the gas sensor element and the connection terminals, wherein
the cover has (i) a connector portion having an opening which allows an external connector to be inserted thereinto and removed therefrom in a predetermined direction, and has (ii) a connector terminal member that is separate from the connector portion and inserted into the opening, and
the connector terminal member has a plurality of connector terminals electrically connected to the respective connection terminals, and an insulator integrally molded with the connector terminals and adapted to insulate the connector terminals from one another.

2. The gas sensor according to claim 1, wherein the connector terminals are bent.

3. The gas sensor according to claim 1, wherein the insulator has a flange portion which traces an inner surface of the opening.

4. A method for manufacturing the gas sensor as claimed in claim 1, comprising:
a connector-terminal-member insertion step of inserting the connector terminal member having a plurality of connector terminals and the insulator integrally molded with the connector terminals and adapted to insulate the connector terminals from one another, into the opening of the cover from the predetermined direction so as to insert the connector terminal member into the cover in a state in which the connector terminals are electrically connected to the respective connection terminals.

5. The method for manufacturing a gas sensor according to claim 4, further comprising:
an integration molding step of insert-molding, to the insulator, a connector terminal cluster in which a plurality of the connector terminals are integrally connected to a joint at their one ends so as to be held and spaced apart from one another, for integrally molding the insulator with the connector terminal cluster in a condition in which the joint is exposed, and
a joint cutting-off step of cutting off, from the connector terminals, the joint which has been exposed in the integration molding step, thereby yielding the connector terminal member.

6. The gas sensor according to claim 1, wherein the cover integrally has a connector portion having an opening orthogonal to the axial direction which allows an external connector to be inserted thereinto and removed therefrom, and has a connector terminal member which can be inserted into the opening.

* * * * *